(12) United States Patent
Tu et al.

(10) Patent No.: US 6,245,067 B1
(45) Date of Patent: Jun. 12, 2001

(54) ABLATION DEVICE AND METHODS HAVING PERPENDICULAR ELECTRODES

(75) Inventors: Hosheng Tu, Tustin; Weng-Kwen Raymond Chia, Irvine, both of CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/193,088

(22) Filed: Nov. 16, 1998

Related U.S. Application Data

(63) Continuation-in-part of application No. 08/834,373, filed on Apr. 16, 1997, now Pat. No. 5,843,020.

(51) Int. Cl.⁷ .................................................. A61B 18/18
(52) U.S. Cl. ............................................. 606/41; 607/101
(58) Field of Search .................................. 606/41, 42, 45, 606/47–50; 607/101, 102; 604/22

(56) References Cited

U.S. PATENT DOCUMENTS

| | | | |
|---|---|---|---|
| 5,810,806 | * | 9/1998 | Ritchart et al. ........................ 606/45 |
| 5,843,020 | * | 12/1998 | Tu et al. ................................ 604/22 |
| 5,876,340 | * | 3/1999 | Tu et al. ............................... 600/439 |
| 5,902,300 | * | 5/1999 | Hahnen et al. ........................ 606/46 |
| 5,906,615 | * | 5/1999 | Thompson ............................. 606/45 |
| 5,947,962 | * | 9/1999 | Guglielmi et al. ..................... 606/32 |
| 5,980,516 | * | 11/1999 | Mulier et al. .......................... 606/41 |
| 5,980,563 | * | 11/1999 | Tu et al. ............................... 607/113 |

* cited by examiner

*Primary Examiner*—Michael Peffley

(57) ABSTRACT

An ablation catheter comprising a delivery catheter and an inner insert having a retractable tip section, wherein a deployable two-piece electrode means is mounted on the retractable tip section and wherein the second piece of the two-piece electrode means is in a circular shape which plane is essentially perpendicular to the delivery catheter, adapted for delivering RF ablative energy to the electrode means.

10 Claims, 7 Drawing Sheets

ABLATION DEVICE AND METHODS HAVING PERPENDICULAR ELECTRODES

This is a continuation-in-part of U.S. Ser. No. 08/834,373, filed Apr. 16, 1997 now U.S. Pat. No. 5,843,020, granted Dec. 1, 1998.

FIELD OF THE INVENTION

The present invention generally relates to improved constructions for tissue ablation systems. More particularly, this invention relates to devices and methods for treatment and reduction of body tissues, such as tumors by simultaneously encircling the tumor with a sharp edge electrode and applying RF energy for ablation. The device penetrates through normal tissue or passes through a natural body opening to reach the target tissue to be treated and delivers therapeutic energy to the target tissue while loosens the target tissue for improved treatment. This device is suitable for reducing the mass of any type of tissue, and it is most particularly useful for treating tissues containing tumor cells and the like.

BACKGROUND OF THE INVENTION

The most popular tumor management approach is through surgical means. Surgical treatment of cellular tissues usually exposes both the target and intervening tissues to substantial trauma and causes a great deal of damage to healthy tissues. During a surgical procedure, precise placement of a treatment device is difficult because of the location of a target tissue in the body or the proximity of the target tissue to obstructions or easily damaged critical body organs, such as nerves or blood vessels. New products with an emphasis on minimally invasive approaches are being progressively developed to replace the traumatic nature of traditional surgical procedures.

There has been a relatively significant amount of activity in the area of high energy as a tool for treatment of tumors. It is known that elevating the temperature of tumors is helpful in the treatment and management of cancerous tissues. The mechanisms of selective cancer cell eradication by high-energy doses are not completely understood. However, Edwards et al. in U. S. Pat. No. 5,536,267 hypothesized certain cellular effects of high energy on cancerous tissues. Nevertheless, treatment methods for applying heat to tumors include the use of direct contact radiofrequency (RF) applicators, microwave radiation, inductively coupled RF fields, ultrasound, and a variety of other simple thermal conduction techniques.

In an illustrative example, high frequency currents are used in electrocautery procedures for cutting human tissues, especially when a bloodless incision is desired or when the operating site is not accessible with a normal scalpel but presents an access for a thin instrument through natural body openings such as the esophagus, intestines, uterus, or urethra. Examples include the removal of prostatic adenomas, bladder tumors or intestinal polyps. In such cases, the high frequency current is fed by a surgical probe into the tissue to be cut. The resulting dissipated heat is controlled so that no boiling and vaporization of the cell fluid occurs at this point. The frequency of the current for this use must be above ca. 300 kHz in order to avoid any adverse effect such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy that is rapidly dissipated and reduced to a non-destructive level by conduction and convection forces of natural body process. Ablative energy may also be controlled by a closed-loop temperature control mechanism.

The same is true for ablation of the tumor itself through the use of RF energy. Different methods have been utilized for the RF ablation of masses such as tumors. Instead of heating the tumors it is ablated through the application of RF energy. This process has been difficult to achieve due to a variety of factors, such as access site, probe location, electrode positioning, energy level, et al. Among them, the most critical factor is the positioning of the RF ablation electrode to effectively ablate all of the mass by controlled delivery and monitoring of RF energy to achieve successful ablation without damage to non-tumor tissue.

There have been a number of different treatment methods and devices for minimally invasively treating tumors. One such example is an endoscope that produces RF hyperthermia in tumors, as described in U.S. Pat. No. 4,920,978. In U.S. Pat. No. 4,920,978, an endoscope for RF hyperthermia is disclosed. In U.S. Pat. No. 4,565,200, an electrode system is described in which a single entrance tract cannula is used to introduce an electrode into a selected body site. In U.S. Pat. No. 5,458,597, a RF probe with fluid infusion capability is described. Similarly, in U.S. Pat. No. 5,536,267, a multiple electrode ablation apparatus with fluid infusion means is described. For the system with a closed-loop temperature control mechanism, the fluid infusion means for the sole purpose of cooling off the tissues may not be required. Recent clinical studies have indicated that the delivered RF energy is rapidly dissipated and reduced to a non-destructive level by conduction and convection forces of natural body process. In all examples, the tissue destruction energy and/or substances have been used to destroy malignant, benign and other types of cells and tissues from a variety of anatomic sites and organs. Tissues treated include isolated carcinoma masses and target tissues in organs such as prostate, glandular and stromal nodules characteristic of benign prostate hyperplasia.

There is a need for a RF ablation apparatus that is useful for treatment and reduction of undesired body tissues by minimally invasive procedures. It would be desirable for such a device to surround the tumor with treatment electrodes in an essentially circular fashion, and to define a controlled ablation amount of RF energy by monitoring the temperature and controlling the energy delivered.

SUMMARY OF THE INVENTION

One object of the present invention is to provide an improved ablation catheter that can be used in ablating a desired tissue mass, such as a tumor, in a minimally invasive manner. In one embodiment, a RF ablation catheter system has a delivery catheter with distal and proximal ends wherein a semi-flexible insert is located within the lumen of said delivery catheter. A handle is attached to the proximal end of the delivery catheter. The semi-flexible insert that is also semi-rigid is like a wire which is made of a conductive material, such as a high strength stainless steel and has a cross-sectional shape of circular, oval, trapezoid, diamond, or rectangular. In a further embodiment, the semi-flexible insert serves as a conducting means for the distal electrode means to be connected to an external RF generator for RF energy transmission. It also serves as a semi-rigid mechanical support in advancing the ablation catheter during catheter insertion and RF ablating operations. The proximal end of said insert is attached to a push-pull mechanism or other deployment mechanism on the handle.

The delivery catheter has an electrode deployment means. The electrode deployment means includes a retractable tip section, which constitutes the distal part of said semi-flexible insert, comprising a farther distal deployable electrode that may be joined to the tip section with a spring-loaded joint. The catheter system has a two-piece electrode means mounted at the distal end of the insert, wherein the two-piece electrode means has a first piece connected to the distal end of the insert and a second piece coupled to the first piece, each piece of the two-piece electrode means having its own distal and proximal ends, wherein the second piece forms an essentially a circular shape. In one embodiment, said electrode means is consisted of a circular electrode having blunt sides all around and the circular plane of the electrode is essentially perpendicular to the delivery catheter. The tip section has a non-deployed state when it is positioned inside the delivery catheter. This non-deployed state is maintained during a catheter insertion step into a patient and during catheter withdrawal from a patient.

In a preferred embodiment, the delivery catheter comprises an inflatable balloon at its distal section. The inflated balloon is adapted to support the second piece when the two-piece electrode means is deployed. A working fluid is used to inflate the balloon.

In another embodiment, the tip section has a distended deployed state when it is advanced out of the distal end of said delivery catheter. In one embodiment, deployment of the retractable tip section is accomplished by a pushing action on the push-pull mechanism on the handle. The deployed tip section has a preformed shape so that the tip section would extend outwardly to one side of said delivery catheter when deployed. In an alternate embodiment, the distal deployed electrode has a pre-installed torsion spring so that the electrode bends inwardly to the opposite side of the delivery catheter. The deployed electrode defines an ablation target along with the forward side of said electrode having a circular shape. In still another embodiment, a portion of said forward side of the deployed electrode has an essentially even edge. In a further embodiment, a portion of the second piece of the two-piece electrode means is made of a conductive material. The portion of the second piece of the two-piece electrode means made of a conductive material is enclosed within an inflatable balloon means. The inflatable balloon in this invention is made of a material selected from the group of polyethylene, polyethylene terephthalate, nylon, silicone, polyurethane, polypropylene, polyimide, cross-linked polyethylene, latex, and semi-permeable membranes.

A conducting wire which is soldered to the proximal end of said insert passes through the interior void of the handle and is thereafter soldered to a contact pin of the connector at the proximal end of the handle. Therefrom, the conducting wire is connected to an external RF current generator for ablation operations. The ablation catheter may further comprise a steering mechanism at the handle for controlling the deflection of the distal section of the delivery catheter. Usually a rotating ring or a secondary push-pull plunger on the handle is employed as an integral part of the steering mechanism. One end of the steering wire is attached at a point on the tip section of said insert while the other end is attached to the steering mechanism at the handle. The steering mechanism on a steerable catheter device is well known to those who are skilled in the art. In an additional embodiment, the ablation catheter further comprises a temperature sensing and closed-loop temperature control mechanism for the electrode having a temperature sensor at the tissue contact site. The location of the temperature sensor is preferably in the proximity of the electrode means.

The delivery catheter of said ablation catheter system of this invention having a tip section under a non-deployed state is inserted into the body through a small surgery hole or through the natural body openings such as esophagus, intestines, uterus, or urethra. Once approaching the target tissue, the tip section is deployed by activating the electrode deployment means at the handle. Once positioning the two-piece electrode means, encircle the target tissue. By a simultaneous or alternate mode, gradually push forward the delivery catheter from the handle against the target tissue and apply RF energy to the electrode means.

The method and apparatus of the present invention have several significant advantages over known ablation catheters or ablation techniques. In particular, the electrode of an ablation catheter of this invention results in a more effective means for reducing the mass of any type of tissue containing tumor cells and the like.

BRIEF DESCRIPTION OF THE DRAWINGS

The features and objects of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
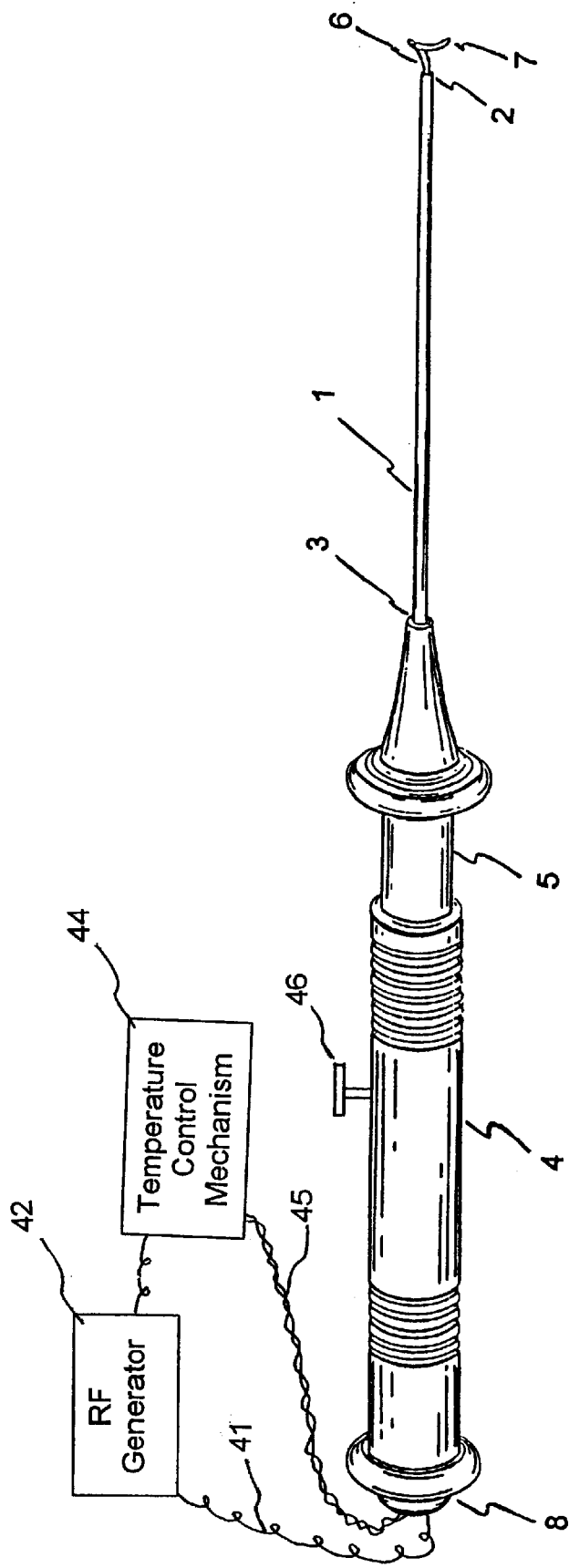
FIG. 1 is a prospective view of the ablation catheter having an electrode deployment means comprising a retractable tip section in accordance with the principles of the present invention.

An ablation catheter constructed in accordance with the principles of the present invention comprises a delivery catheter with distal and proximal ends wherein a semi-flexible insert is located within the lumen of said delivery catheter. FIG. 1 shows a prospective view of the catheter system having a delivery catheter 1 with a distal end 2, a proximal end 3, and at least one lumen 15 extending between the distal end 2 and the proximal end 3. A semi-flexible insert 9 is located inside the at least one lumen 15 of the delivery catheter 1, wherein the insert has a distal end, a proximal end, and an elongate shaft extending therebetween. The insert 9 has a retractable tip section.

The proximal end of a semi-flexible insert is attached on a push-pull mechanism 5 at the handle 4. The distal end of said insert 9 comprises a two-piece electrode means consisting of an outwardly extended first piece 31 and a farther second piece 32 that is joined to said first piece 31 by a spring-loaded joint 10. The semi-flexible insert 9 serves as a conducting means for the electrode to be connected to an external RF generator 42. Said insert 9 also serves as a mechanical support in advancing the ablation catheter during catheter insertion operation and during RF ablating operation.

A two-piece electrode means is mounted at the distal end of the insert 9, wherein the two-piece electrode means has a first piece 31 connected to the distal end of the insert 9 and a second piece 32 coupled to the first piece 31. Each piece of the two-piece electrode means has its own distal and proximal ends, wherein the second piece 32 forms an essentially circular shape;

A handle 4 is attached to the proximal end 3 of the delivery catheter 1, wherein the handle has a cavity.

An electrode deployment means 5 is located at the handle, wherein the electrode deployment means is connected to the proximal end of the insert 9. A preformed shape is adapted for the two-piece electrode means of the retractable tip section. The first piece 31 extends outwardly to one side of the delivery catheter 1 when the electrode means is deployed, wherein the second piece 32 bends inwardly to the opposite side of the delivery catheter 1 to expose the second piece 7 essentially perpendicular or at a sharp angle to the delivery catheter 1.

An insulated conducting wire 41 which is secured to the proximal end of said semi-flexible insert 9 passes through the interior void of the handle 4 and is thereafter secured to a contact pin of a connector 8 at the proximal end of said handle 4. From there, the conducting wire 41 is connected to an external RF generator 42 for RF energy transmission. In a further embodiment, the ablation catheter may comprise a steering mechanism at the handle for controlling the deflection of the distal section of the delivery catheter 1. One end of the steering wire is attached at certain point of the tip section of said insert while the other end is attached to the steering mechanism at the handle. The steering mechanism on a steerable catheter is well known to those who are skilled in the art.

In an additional embodiment, the ablation catheter further comprises a temperature sensor 43, a temperature sensing wires 45, and a closed-loop temperature control mechanism 44 for the electrode means 7 having a temperature sensor 43 at the tissue contact site of said electrode 7.

Figure 2:
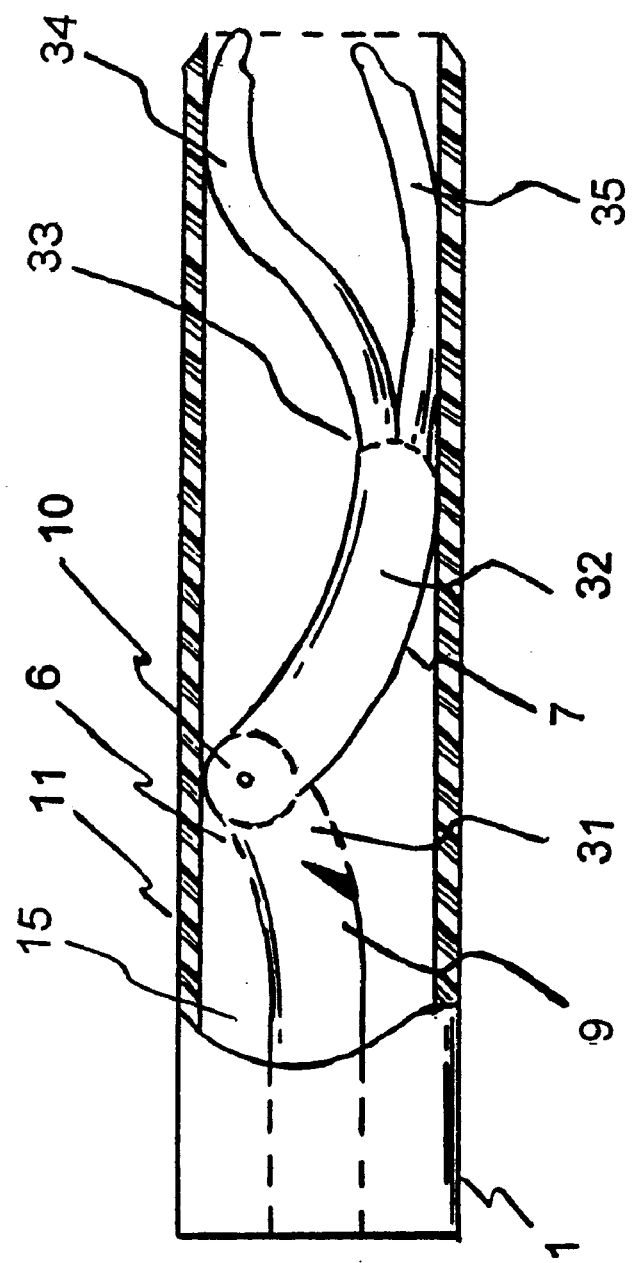
FIG. 2 is a closed-up view of the retractable tip section at a non-deployed state.

FIG. 2 is a close-up view of the retractable tip section at a non-deployed state. The semi-flexible insert 9, having a retractable tip section 6, is located within the lumen 15 of the delivery catheter 1. A deployable electrode means 7, a two-piece electrode comprising a first piece 31 and a second piece 32 joined by a torsion spring 10, is located at the farther distal end of said tip section 6. The non-deployed state is maintained during catheter insertion into a patient and catheter withdrawal from a patient. Said torsion spring is positioned at the joint in a way that the spring-loaded force pushes the electrode backward when deployed. Other suitable joint means is also applicable to finction as a joint 10. In another embodiment, the distal section 11 of said delivery catheter 1 comprises a reinforced shaft to maintain its circular cross-section shape even under the impact of the preformed tip section 6 and/or pre-installed spring-loaded electrode means 7. Reinforcement of the distal shaft of said catheter system could be accomplished either by a braided tubing or a tubing with higher hardness fused to said delivery catheter 1. The second piece 32 further comprises two branches 34 and 35 at its distal end 33. The preshaped branches 34 and 35 are part of the two-piece electrode means 7.

Figure 3:
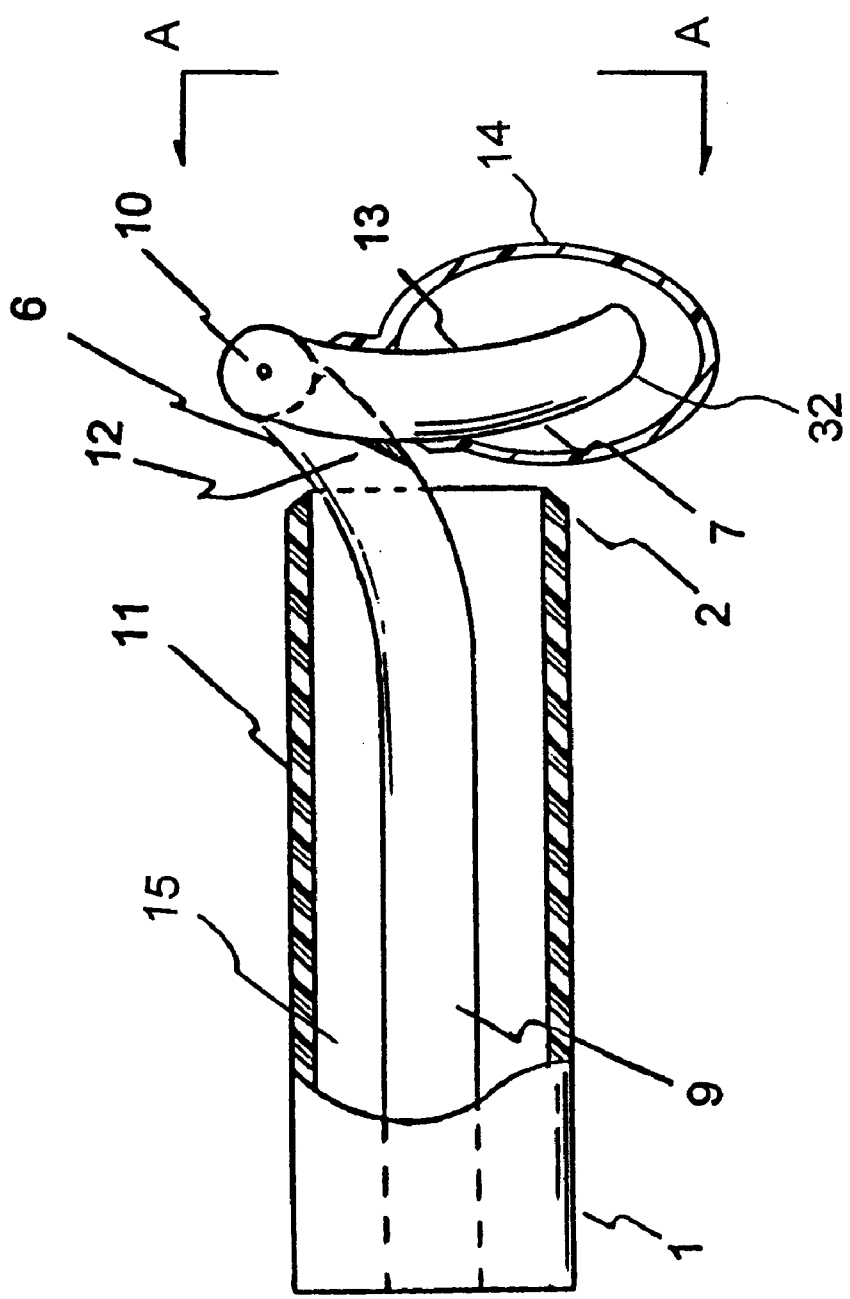
FIG. 3 is a closed-up view of the retractable tip section at a fully deployed state.
Figure 6:
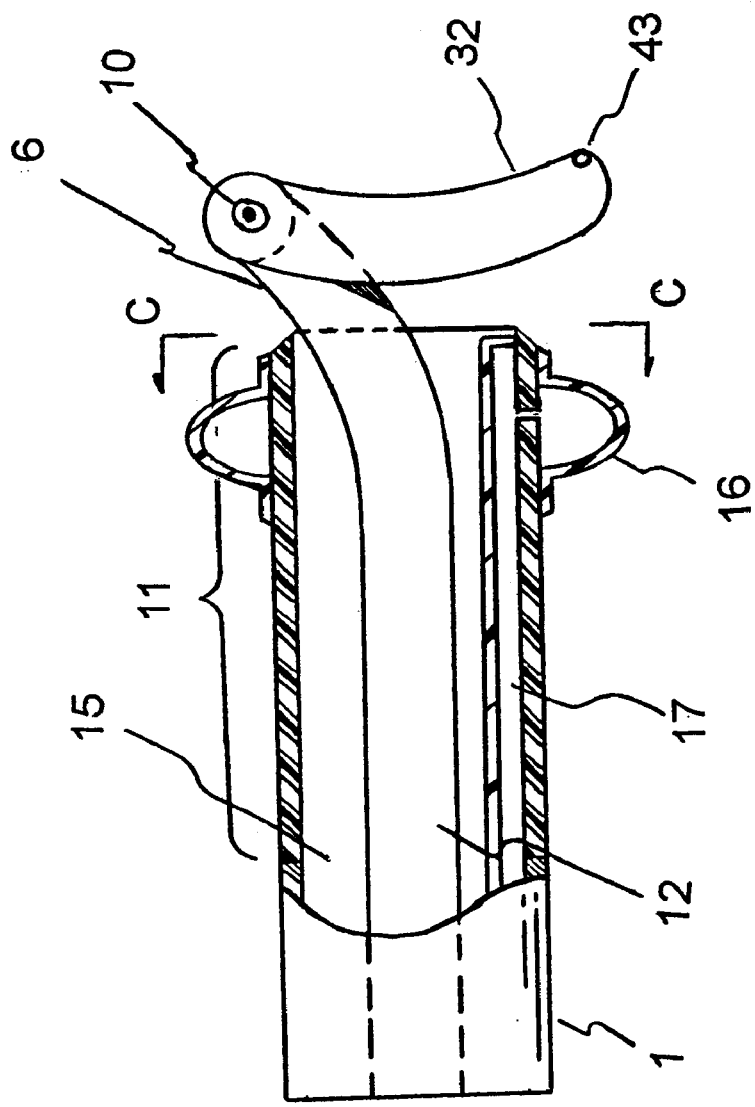
FIG. 6 is a closed-up view of the retractable tip section of a preferred embodiment of the present invention having an inflatable balloon.

FIG. 3 shows a close-up view of said retractable tip section at a fully deployed state. The tip section 6 has a distended deployed state when it is advanced out of the distal end 2 of said delivery catheter 1. Deployment of the tip section is accomplished by a pushing action on the push-pull mechanism 5 at the handle 4. Because of its preformed shape, the first piece 31 of the two-piece electrode means extends outwardly to one side of said catheter when deployed. In the meantime, the second piece 32 of the two-piece electrode means 7 bends inwardly to the opposite side of said catheter because of its pre-installed torsion spring 10 or other applicable means. Each piece 31 or 32 has its own distal and proximal ends. The spring-loaded electrode means can only bend to certain position when fully deployed because of a lower stopper 12 on the tip section 6. At a fully deployed state, the second piece 32 of the two-piece electrode means 7 is essentially perpendicular or at a sharp angle to the delivery catheter 1. An alternate method for stopping the second piece 32 is by an inflated balloon means as shown in FIG. 6.

In one preferred embodiment, a portion 13 of the second piece 32 of the two-piece electrode means 7 is made of a conductive material, wherein the conductive material is enclosed within an inflatable balloon means 14. The inflatable balloon is preferably made of a material selected from the group of polyethylene, polyethylene terephthalate, nylon, silicone, polyurethane, polypropylene, polyimide, cross-linked polyethylene, latex, and semi-permeable membranes. The balloon 14 is inflated by a working fluid, wherein the working fluid may preferably be a hot fluid. Balloon construction on a catheter is well known to one who is skilled in the art.

The location of a temperature sensor 43 is preferably in the proximity of the electrode means. Temperature sensing wires 45 along with a thermocouple or thermister means are provided to transmit the temperature data from the tissue contact site to an external temperature measuring and control device 44. An algorithm is installed in said measuring and control device so that a closed-loop temperature control is effective and the temperature data is relayed to the RF generator 42 for controlled energy delivery.

Figure 4:
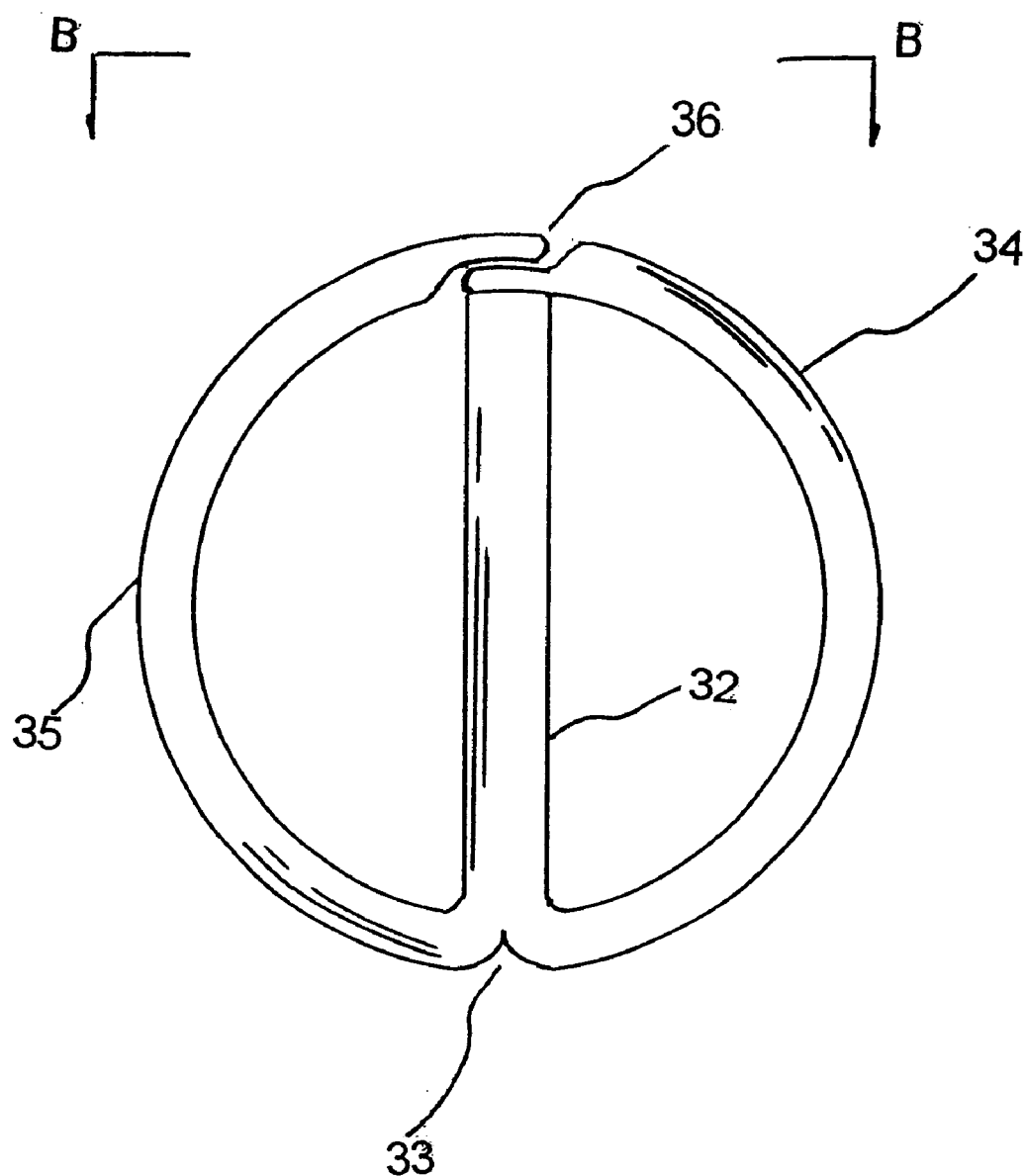
FIG. 4 is a cross-sectional view of the deployed electrode means having a circular shape on its front side of FIG. 3, section A—A.

FIG. 4 shows a cross-sectional view of the deployed electrode means having a circular shape on its front side of FIG. 3 section A—A. The branches 34 and 35 form a circular shape, wherein the ends of the two branches 34 and 35 meet at point 36 to form a complete circle.

Figure 5:
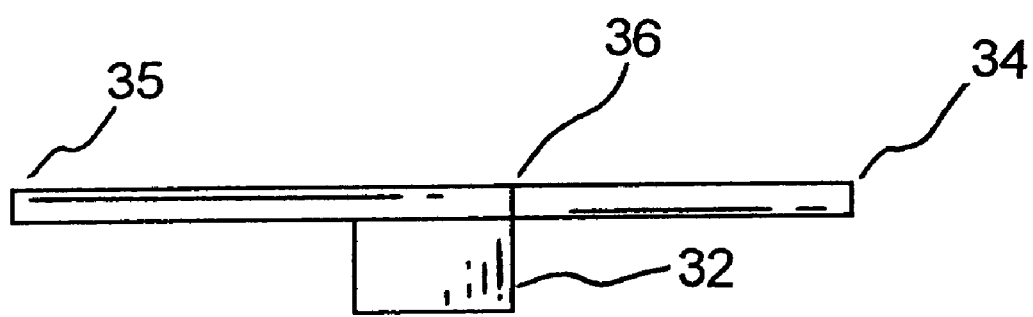
FIG. 5 is a cross-sectional view of the deployed electrode means having a circular shape on its front side of FIG. 4, section B—B.

FIG. 5 shows a cross-sectional view of the deployed electrode means having a circular shape on its front side of FIG. 4 section B—B. When the branches 34 and 35 contact a tissue and deliver RF energy, it forms a complete circular lesion. The plane formed by branches 34 and 35 is essentially perpendicular to or at a sharp angle to the delivery catheter 1.

FIG. 6 shows a close-up view of the retractable tip section of a preferred embodiment of the present invention having an inflatable balloon 16 at the distal tip section of the delivery catheter 1. A separate fluid lumen 17 within the delivery catheter 1 is employed for conveying a working fluid for balloon inflation purposes. The inflated balloon 16 is used as a layback support for the electrode means 7 comprising the branches 34 and 35.

Figure 7:
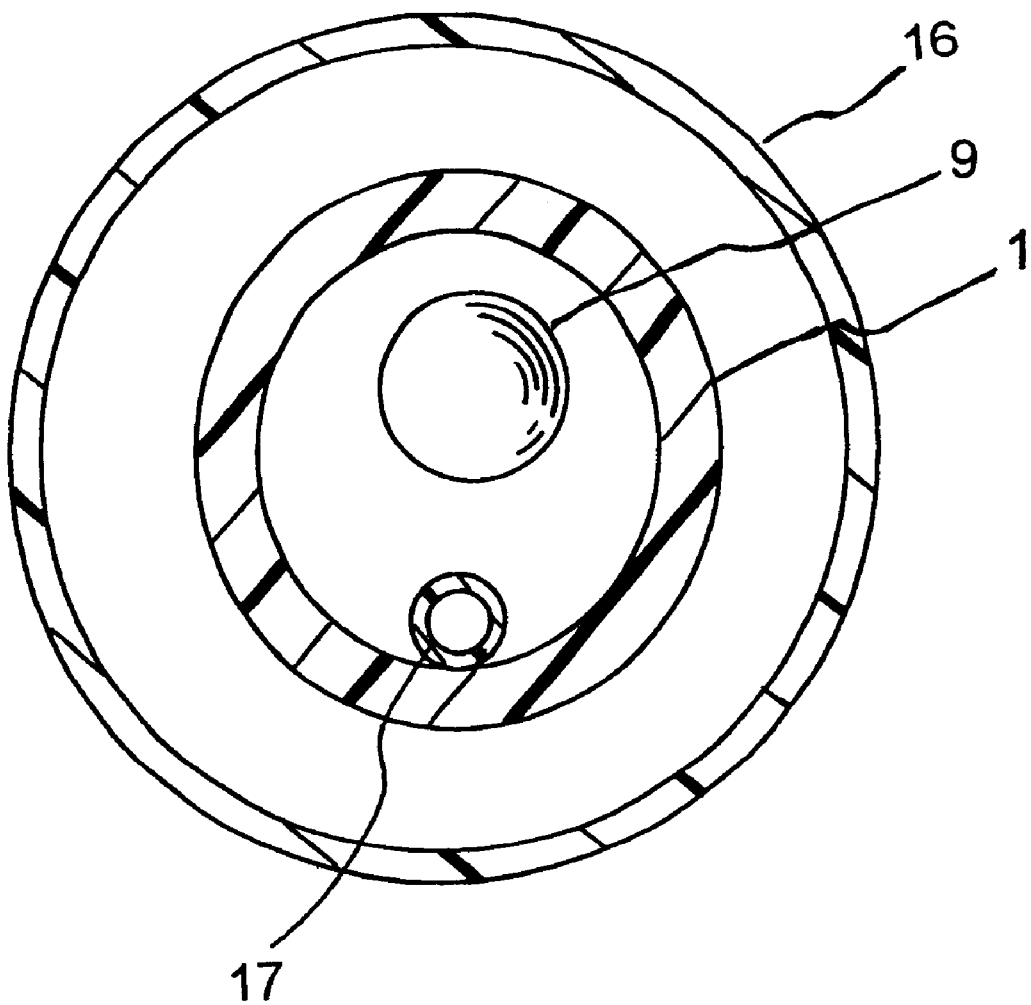
FIG. 7 is a cross-sectional view of the distal end of the delivery catheter, section C—C of FIG. 6.

FIG. 7 shows a cross-sectional view of the distal end of the delivery catheter, section C—C of FIG. 6. The fluid conduit 17 is located within the delivery catheter 1. The balloon 16 is inflated by a working fluid through the fluid conduit 17 to the lumen of the balloon 16.

A method for operating an ablation catheter system inside a body of a patient for treating a target tissue is illustrated. The ablation catheter system comprises a delivery catheter having a distal section, a distal end, a proximal end, and at least one lumen extending between the distal end and the proximal end; a semi-flexible insert located inside the at least one lumen of the delivery catheter, wherein the insert has a distal end, a proximal end, and an elongate shaft extending therebetween, and wherein the insert has a retractable tip section; a two-piece electrode means mounted at the distal end of the insert, wherein the two-piece electrode means has a first piece connected to the distal end of the insert and a second piece coupled to the first piece, each piece of the two-piece electrode means having its own distal and proximal ends, wherein the second piece forms an essentially a circular shape; a handle attached to the proximal end of the delivery catheter, wherein the handle has a cavity; an electrode deployment means located at the handle, wherein the electrode deployment means is connected to the proximal end of the insert; and a preformed shape for the two-piece electrode means of the retractable tip section, wherein the first piece extends outwardly to one side of the delivery catheter when the electrode means is deployed, and wherein the second piece bends inwardly to the opposite side of the delivery catheter to expose the second piece essentially perpendicular to the delivery catheter; and a RF generator The method comprising the steps of: (a) introducing the delivery catheter having an insert under a non-deployed state into the body through a small surgery hole or through a natural body opening; (b) once approaching the target tissue, deploying the tip section by activating the electrode deployment means at the handle; (c) once positioning the two-piece electrode means, encircling the target tissue; and (d) by a simultaneous or alternate mode, gradually pushing forward the delivery catheter from the handle against the target tissue and applying RF energy to the electrode means.

The method for operating the ablation catheter system further comprises a temperature sensor mounted at the electrode means and a closed-loop temperature control mechanism, wherein the temperature measured by the temperature sensor is relayed to the closed-loop temperature control mechanism and adapted for controlling the RF current delivery to the electrode means.

Alternately, a method for operating an ablation catheter system inside a heart of a patient for treating a target tissue is illustrated. The ablation catheter system comprises a delivery catheter having a distal section, a distal end, a proximal end, and at least one lumen extending between the distal end and the proximal end, wherein an inflatable balloon is mounted at the distal section of the delivery catheter; a semi-flexible insert located inside the at least one lumen of the delivery catheter, wherein the insert has a distal end, a proximal end, and an elongate shaft extending therebetween, and wherein the insert has a retractable tip section; a two-piece electrode means mounted at the distal end of the insert, wherein the two-piece electrode means has a first piece connected to the distal end of the insert and a second piece coupled to the first piece, each piece of the two-piece electrode means having its own distal and proximal ends, wherein the second piece forms an essentially a circular shape; a handle attached to the proximal end of the delivery catheter, wherein the handle has a cavity; an electrode deployment means located at the handle, wherein the electrode deployment means is connected to the proximal end of the insert; and a preformed shape for the two-piece electrode means of the retractable tip section, wherein the first piece extends outwardly to one side of the delivery catheter when the electrode means is deployed, and wherein the second piece bends inwardly to the opposite side of the delivery catheter to expose the second piece essentially perpendicular to the delivery catheter; and a RF generator. The method comprises the steps of (a) introducing the delivery catheter having an insert under a non-deployed state into the heart through a natural body opening; (b) once approaching the target tissue inside a chamber of the heart, deploying the tip section by activating the electrode deployment means at the handle; (c) once positioning the two-piece electrode means, encircling the target tissue; (d) inflating the balloon with a working fluid; and (e) applying RF energy to the electrode means.

While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:

a delivery catheter having a distal section, a distal end, a proximal end, and at least one lumen extending between the distal end and the proximal end;

a semi-flexible insert located inside the at least one lumen of the delivery catheter, wherein the insert has a distal end, a proximal end, and an elongate shaft extending therebetween, and wherein the insert has a retractable tip section;

a two-piece electrode means mounted at the distal end of the insert, wherein the two-piece electrode means has a first piece connected to the distal end of the insert and a second piece coupled to the first piece, each piece of the two-piece electrode means having its own distal and proximal ends, wherein the second piece forms an essentially circular shape, wherein a portion of the second piece of the two-piece electrode means made of a conductive material is enclosed within an inflatable balloon means;

a handle attached to the proximal end of the delivery catheter, wherein the handle has a cavity;

an electrode deployment means located at the handle, wherein the electrode deployment means is connected to the proximal end of the insert; and a preformed shape for the two-piece electrode means of the retractable tip section, wherein the first piece extends outwardly to one side of the delivery catheter when the electrode means is deployed, and wherein the second piece bends inwardly to the opposite side of the delivery catheter to expose the second piece essentially perpendicular to the delivery catheter.

2. The catheter system as in claim 1, wherein the inflatable balloon is made of a material selected from the group of polyethylene, polyethylene terephthalate, nylon, silicone, polyurethane, polypropylene, polyimide, cross-linked polyethylene, latex, and semi-permeable membranes.

3. The catheter system of claim 1 further comprising an inflatable balloon at the distal section of the delivery catheter.

4. The catheter system as in claim 3, wherein the inflatable balloon is made of a material selected from the group of polyethylene, polyethylene terephthalate, nylon, silicone, polyurethane, polypropylene, polyimide, cross-linked polyethylene, latex, and semi-permeable membranes.

5. A method for operating an ablation catheter system inside a body of a patient for treating a target tissue, the ablation catheter system comprising: a delivery catheter having a distal section, a distal end, a proximal end, and at least one lumen extending between the distal end and the proximal end; a semi-flexible insert located inside the at least one lumen of the delivery catheter, wherein the insert has a distal end, a proximal end, and an elongate shaft extending therebetween, and wherein the insert has a retractable tip section; a two-piece electrode means mounted at the distal end of the insert, wherein the two-piece electrode means has a first piece connected to the distal end of the insert and a second piece coupled to the first piece, each piece of the two-piece electrode means having its own distal and proximal ends, wherein the second piece forms an essentially a circular shape, wherein a portion of the second piece of the two-piece electrode means made of a conductive material is enclosed within an inflatable balloon means; a handle attached to the proximal end of the delivery catheter, wherein the handle has a cavity; an electrode deployment means located at the handle, wherein the electrode deployment means is connected to the proximal end of the insert; and a preformed shape for the two-piece electrode means of the retractable tip section, wherein the first piece extends outwardly to one side of the delivery catheter when the electrode means is deployed, and wherein the second piece bends inwardly to the opposite side of the delivery catheter to expose the second piece essentially perpendicular to the delivery catheter; and a RF generator; the method comprising the steps of:

(a) introducing the delivery catheter having an insert under a non-deployed state into the body through a small surgery hole or through a natural body opening;

(b) once approaching the target tissue, deploying the tip section by activating the electrode deployment means at the handle;

(c) once positioning the two-piece electrode means, encircling the target tissue; and (d) by a simultaneous or alternate mode, gradually pushing forward the delivery catheter from the handle against the target tissue and applying RF energy to the electrode means.

6. The method for operating an ablation catheter system as in claim 5, further comprising a step of inflating the balloon with a working fluid.

7. The method for operating an ablation catheter system as in claim 6, wherein the working fluid is a hot fluid.

8. A method for operating an ablation catheter system inside a heart of a patient for treating a target tissue, the ablation catheter system comprising: a delivery catheter having a distal section, a distal end, a proximal end, and at least one lumen extending between the distal end and the proximal end, wherein an inflatable balloon is mounted at the distal section of the delivery catheter; a semi-flexible insert located inside the at least one lumen of the delivery catheter, wherein the insert has a distal end, a proximal end, and an elongate shaft extending therebetween, and wherein the insert has a retractable tip section; a two-piece electrode means mounted at the distal end of the insert, wherein the two-piece electrode means has a first piece connected to the distal end of the insert and a second piece coupled to the first piece, each piece of the two-piece electrode means having its own distal and proximal ends, wherein the second piece forms an essentially a circular shape; a handle attached to the proximal end of the delivery catheter, wherein the handle has a cavity; an electrode deployment means located at the handle, wherein the electrode deployment means is connected to the proximal end of the insert; and a preformed shape for the two-piece electrode means of the retractable tip section, wherein the first piece extends outwardly to one side of the delivery catheter when the electrode means is deployed, and wherein the second piece bends inwardly to the opposite side of the delivery catheter to expose the second piece essentially perpendicular to the delivery catheter; and a RF generator; the method comprising the steps of:

(a) introducing the delivery catheter having an insert under a non-deployed state into the heart through a natural body opening;

(b) once approaching the target tissue inside a chamber of the heart, deploying the tip section by activating the electrode deployment means at the handle;

(c) once positioning the two-piece electrode means, encircling the target tissue;

(d) inflating the balloon with a working fluid; and (e) applying RF energy to the electrode means.

9. The method for operating an ablation catheter system of claim 8 further comprising a temperature sensor mounted at the electrode means and a closed-loop temperature control mechanism, wherein the temperature measured by the temperature sensor is relayed to the closed-loop temperature control mechanism and adapted for controlling the RF current delivery to the electrode means.

10. The method for operating an ablation catheter system as in claim 8, wherein the inflatable balloon is made of a material selected from the group of polyethylene, polyethylene terephthalate, nylon, silicone, polyurethane, polypropylene, polyimide, cross-linked polyethylene, latex, and semi-permeable membranes.

* * * * *